United States Patent [19]

Holcombe et al.

[11] Patent Number: 4,529,307
[45] Date of Patent: Jul. 16, 1985

[54] METHOD AND APPARATUS FOR CONCENTRATING A SELECTED ELEMENT FOR ATOMIC SPECTROSCOPY

[75] Inventors: James A. Holcombe; Thomas Rettberg, both of Austin, Tex.

[73] Assignee: Board of Regents, The University of Texas System, Austin, Tex.

[21] Appl. No.: 482,066

[22] Filed: Apr. 5, 1983

[51] Int. Cl.³ .............................................. G01N 21/74
[52] U.S. Cl. ...................................... 356/312; 356/244
[58] Field of Search ........................... 356/312, 244, 36

[56] References Cited

U.S. PATENT DOCUMENTS 3,957,374 5/1976 Kriese et al. .
3,979,162 9/1976 George .
4,162,849 7/1979 Huber .
4,295,854 10/1981 Huber .

OTHER PUBLICATIONS

Chakrabarti, C.; Wan, C.; Hamed, H.; and Bertels, P. "The Way to an Absolute Method of Analysis by Capacitive Discharge Technique in Graphite Furnace Atomic Absorption Spectrophotometry" Candian Research, May, 1980, at 31-34.

L'vov, B. "Electrothermal Atomization, The Way Toward Absolute Methods of Atomic Absorption Analysis", Reprint of Work Presented as an Invited Paper on Nov. 14-19, 1976.

Holcombe, J. and Sheehan, M. "Graphite Furnace Modification for Second Surface Atomization" Applied Spectroscopy, Nov.-Dec. 1982 at 631.

Primary Examiner—F. L. Evans
Attorney, Agent, or Firm—Arnold, White & Durkee

[57] ABSTRACT

A method and apparatus are disclosed for concentrating a selected element of a sample in a furnace or electrothermal atomizer for atomic spectroscopy. The apparatus includes a heating receptacle comprised of materials capable of withstanding the temperatures of atomization of such a sample. The apparatus further includes a means for heating the receptacle to the temperatures of atomization and a means for selectively cooling a selected location of the receptacle to a temperature below the vaporization temperature of the desired element in order to selectively condense the element at the location. The method includes the steps of heating a sample within a heating chamber to a temperature above the vaporization temperature of the selected element or species containing the selected element, maintaining or cooling a selected location of the heating chamber or furnace to a temperature below the vaporization temperature of the selected element in order to condense the selected element at the desired location, removing much of the remaining vaporized portion of the sample and particulate matter from the heating chamber, and then reheating the selected location to vaporize the element for measurement by spectroscopy.

8 Claims, 5 Drawing Figures

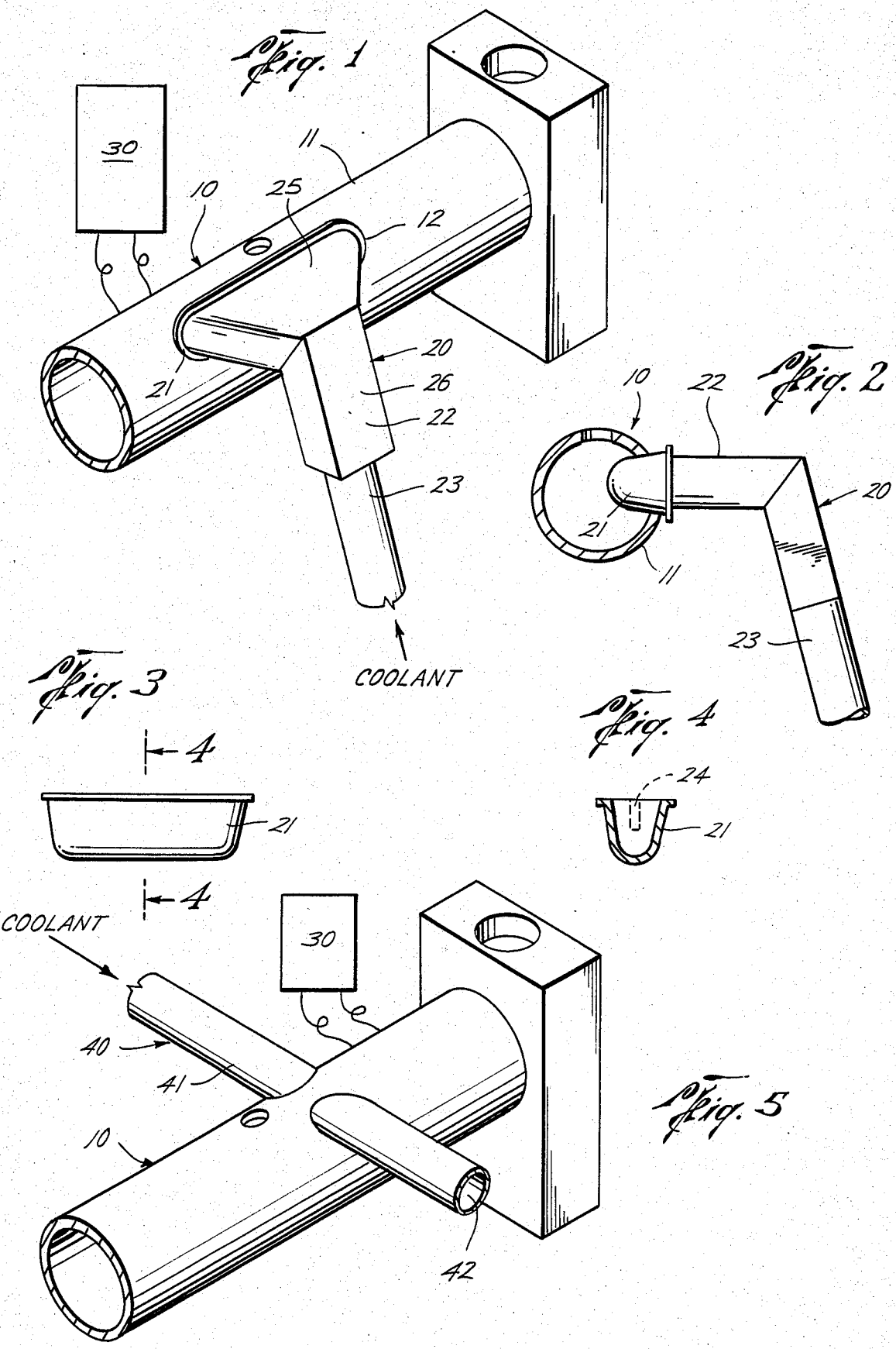

METHOD AND APPARATUS FOR CONCENTRATING A SELECTED ELEMENT FOR ATOMIC SPECTROSCOPY

BACKGROUND OF THE INVENTION

The invention relates to apparatus for atomic spectroscopy, and more specifically, the invention relates to a method and apparatus for concentrating a selected element of a sample in a furnace or electrothermal atomizer for atomic spectroscopy.

There exist several forms of atomic spectroscopy, each of which involves heating a sample to a selected temperature to prepare the sample for a spectroscopic measurement. For example, in atomic absorption spectroscopy, the procedure for preparing and measuring a trace element in a sample may include the steps of gently drying the sample by resistive heating in a furnace and pulse heating the furnace to an extremely high temperature (sometimes in the range of 3000° C.) to atomize the sample. A light beam with selected frequency is then passed through the sample from which quantitative information is obtained by determining the extent of attenuation of the light caused by the presence of the trace material to be measured.

In theory, the measuring beam is attenuated only by atoms of the desired element, those being the atoms which absorb the same spectral lines. The analytical accuracy of this method, as well as the other methods, however, is often impaired when samples in a complex matrix are being analyzed. For example, included among the ways analytical accuracy may be effected are (a) loss of a desired element by prevolatilization as a molecular species; (b) formation of a molecular species containing the element caused by reactions in the gas phase involving the element; (c) uncorrectable molecular absorption or light scattering effects caused by particulate matter in the sample; and (d) non-uniform temperature along the furnace axis while the element is being vaporized.

Pre-volatilization involves the loss of the element at a temperature earlier than one would desire. One approach to avoid this result is to use a "platform" or "microboat", which is usually a piece of graphite laid within the furnace. The sample is deposited on the inserted member and the furnace is heated. Due to poor contact between the platform (or microboat) and the furnace wall, there exists a temperature lag in the heating rate of the inserted graphite and the wall. Thus, when the material is finally vaporized from the platform (or microboat), the inside temperature of the furnace is at a higher value and increases the probability that the element is released by thermal decomposition as a free atomic species.

The use of a platform or microboat, however, does not provide a means of controlling the temperature difference between the platform and the furnace. The microboat, therefore, does not provide a means for selectively vaporizing the element as needed.

With regard to gas phase molecular formation, the use of the platform or microboat assists in dissociating of interfering molecular species. More specifically, the increased gas phase temperature obtained at the time of vaporization promotes thermal dissociation. Because the platform does not provide for the selective vaporization of the sample, however, the extent of dissociation may not be complete. It would therefore be advantageous to be able to retain the element on the platform or microboat until the desired temperature is reached.

Background scatter of molecular absorption is caused by certain molecules absorbing the same wavelength as the element. Scatter can also be caused by the presence of particulate matter ("smoke"). Electronic correction systems using such means as a deuterium lamp or the Zeeman effect have been developed to correct these problems; but these systems are often not adequate and sometimes quite expensive.

Additionally, it is known that conventionally used furnaces often do not heat up uniformly along their length. As a result, the element to be measured often vaporizes and condenses at the cooler regions in the tube. While the use of the platform or microboat has permitted the heating of the furnace to a fairly high temperature before the element is released, it has been found that the temperature is still sometimes not uniform, and that the desired element condenses at the cooler regions. It would therefore be advantageous to be able to control the release of the element such that the sample is vaporized only when the furance is brought to a nearly uniform, high temperature.

Accordingly, it is desirable to provide a system which promotes thermal dissociation of the element to be measured from other molecular species, while at the same time minimizing loss by prevolatilization at a temperature earlier than desired.

SUMMARY OF THE INVENTION

Accordingly, an apparatus is provided for concentrating a selected element of a sample for atomic spectroscopy which includes a heating receptacle comprised of material capable of withstanding the temperatures of atomization of such a sample. The apparatus further includes a means for heating the receptacle to the temperatures of atomization for such a sample and a means for selectively cooling a selected location of the receptacle to a temperature below the vaporization temperature of the desired element in order to selectively condense the element at the location.

In a preferred embodiment of the present invention, the selective cooling means includes an insert member or plug mounted in a wall of the receptacle to provide a condensation location for the selected element. The insert member has a coolant conduit or chamber disposed therein to accommodate the flow of a coolant to cool the member. The cooling means further includes a flow means for selectively passing a coolant through the cooling conduit in order to selectively cool the insert member to a temperature below the vaporization temperature of the selected element.

In an alternative embodiment of the present invention, the insert member comprises a cylindrical tube extending through the receptacle. The tube has a bore extending through it to act as the conduit for the coolant.

The provision of a means for selectively cooling a location in a furnace or atomizer provides several advantages. First, by keeping the temperature of the location slightly below the vaporization point of the desired element to be measured, the element is maintained as condensate on the location while particulate matter and molecular species having a lower vaporization point than the element are removed. At the same time, the furnace can be heated to a high uniform temperature prior to vaporization of the element from the insert member.

The ability to selectively cool a location in the furnace also enables one to first heat the sample to a temperature above the vaporization temperature of the desired element, thus accommodating partial thermal dissociation of undesired molecular species from the selected element, and then condense the selected element onto the cool location, while removing particulate matter and more volatile molecular species from the heated furnace.

More particularly, the present invention provides a method of concentrating a selected element of a sample in a furnace or electrothermal atomizer for atomic spectroscopy. The method includes the steps of heating the sample to a temperature above the vaporization temperature of the selected element or species containing the selected element. A selected location of the heating chamber or furnace is maintained at a temperature below the vaporization temperature of the selected element in order to condense the selected element at the desired location. Much of the remaining vaporized portion of the sample and particulate matter are then removed from the heating chamber. The selected location is then reheated to vaporize the selected element for measurement by spectroscopy.

In a preferred aspect of the method of the present invention, the heating chamber is heated, prior to the reheating of the selected location, to a high, uniform temperature suitable for substantial thermal dissociation of undesirable molecular species which either contain the selected element or spectrally interfere with the detection of the selected element.

Accordingly, the present invention overcomes the prior disadvantages by providing a method and apparatus which enable the partial distillation of a desired element from the sample and the selected release of the element for measurement at a temperature suitable for substantial thermal dissociation as desired.

BRIEF DESCRIPTION OF THE DRAWINGS

This invention will further be illustrated by reference to the appended drawings which illustrate a particular embodiment of the apparatus of the present invention.

FIG. 1 is a sectional perspective view illustrating the apparatus of the present invention.

FIG. 2 is a partial section view of the apparatus shown in FIG. 1.

FIG. 3 is a side view of an insert member utilized in accordance with the present invention.

FIG. 4 is a sectional view of the insert member shown in FIG. 3 taken along line 4—4.

FIG. 5 is a perspective sectional view of an alternative embodiment of the apparatus of the present invention.

DETAILED DESCRIPTION

The present invention is generally represented by a heating chamber 10 to which is mounted a means 20 for selectively cooling a desired location of the chamber. The system further includes a means for heating a sample to desired temperatures which is shown schematically as 30.

Referring to FIG. 1, the heating chamber 10 includes a heating tube 11 comprised of a material suitable for heating a sample to the temperatures of atomization. In the preferred embodiment, the heating tube 11 is a graphite furnace tube. It will be understood, however, that any of a number of heating tubes utilized for spectroscopy may be adapted for use in accordance with the present invention.

The heating tube 11 includes an aperture 12 adapted to receive the selective cooling means 20. In the preferred embodiment, the aperture 12 is configured to form an elongated oval having parallel sides and opposing semi-circular ends.

Referring to FIGS. 1 and 2, the selective cooling means 20 includes an insert member 21 mounted in the aperture 12 of the tube 11, a coolant supply nozzle 22 connected in communication with the insert member 21, and a coolant supply line 23 connected in communication with the supply nozzle 22.

As shown in FIGS. 1-4, the insert member or plug 21 has an elongated oval configuration complementary to the configuration of the aperture 12 of tube 11 such that the insert member 21 may be fit within the aperture 12 in use. In the preferred embodiment the fit between the insert member 21 and the tube 11 is such that conductive heat transfer is minimized between the insert 21 and tube 11. It will be understood that insulation may be provided between the insert member 21 and the tube 11 to minimize heat transfer by conduction, while accommodating a snug fit between the two members, if desired.

The insert member 21 further forms a trough, as shown in cross-section in FIG. 4, which is disposed with the open side to the outside of the tube, as shown in FIG. 2. The trough of the insert member 21 forms a cooling chamber 28 to receive the flow of coolant to cool the plug 21 when in position.

The insert plug 21 may further include a flow divider 24 (shown ghosted in FIG. 4). The flow divider 24 may be disposed to extend longitudinally across the top to the center of the trough and extend downwardly into the trough a sufficient distance to allow flow of coolant under and around the divider to cool the insert member 21 in use.

The coolant supply nozzle 22, in the preferred embodiment, is comprised of two sections, an insert adapter section 25 and a coolant supply line adapter 26, which are angularly connected to direct coolant flow from the coolant supply line 23 to the insert plug 21. The insert adapter section 25 is configured to fit loosely into the top of the insert member 21 to allow venting of coolant between the wall of the insert adapter section 25 and the inside wall of the insert member 21. For those embodiments of the insert member 21 which do not include a means of circulating flow therethrough, this venting is necessary to enable the continuous flow of fresh coolant through the insert member 21.

The coolant line supply adapter 26 is shaped to fit snuggly onto the coolant supply line 23 to form a fluid tight connection between the adapter 26 and the line 23.

The coolant utilized in accordance with the present invention may comprise any of a number of gases, liquids or other fluids suitable for effecting heat transfer to cool the insert 21. In the preferred embodiment, nitrogen or another inert gas at room temperature is used as the coolant.

The means 30 for heating the chamber to a desired temperature may comprise any of a number of suitable heating means currently utilized in atomic spectroscopy. In the embodiment pictured, the heating means 30 comprises a suitable current source adapted for resistive heating of the chamber.

Referring to FIG. 5, there is shown an alternative embodiment of the present invention wherein a hollow tubular member 40 serves as the insert member 21 shown in FIGS. 1-4. In the preferred aspect of this embodiment, the hollow tubular member 40 is comprised of a cylindrical tube 41 which extends through the heating chamber 11 at a selected location. The cylindrical tube 41 has a bore 42 extending therethrough to act as a coolant conduit or chamber for the passage of coolant when desired. As with the heating tube 11, the hollow tubular member 40 is comprised of materials suitable for withstanding the temperatures of atomization of the samples to be tested.

The present invention also comprises a method for concentrating a selected element of a sample in a furnace or electrothermal atomizer for atomic spectroscopy. The method includes the steps of heating the sample within the heating tube 11 to a temperature above the vaporization temperature of the selected element to be concentrated. The coolant is continually supplied to the insert member 21 or tubular member 40 to cool the insert member 21 or tubular member 40 to a temperature below the vaporization temperature of the selected element in order to condense such a selected element at the selected location. The more volatile species which are vaporized and which do not contain the selected element are withdrawn from the heated furnace and not condensed at the selected location. The flow of coolant is then cut off from the insert member 21 whereby the insert member 21 is allowed to heat to approach the temperature of the tube 11 to vaporize the selected element for measurement by spectroscopy.

In a preferred aspect of the present method, the furnace is heated to a sufficient temperature to substantially effect thermal dissociation of undesirable molecular species containing the selected element or other interfering molecular species prior to the heating of the insert member.

The present invention has been disclosed in connection with specific embodiments. However, it will be apparent to those skilled in the art that variations from the illustrated embodiments may be taken without departing from the spirit and scope of the invention. For example, the shape of the tubular member 40 may be varied to any of a number of regular or irregular polygonal shapes in accordance with the present invention. Additionally, a conduit could be adapted directly into the wall of the heating tube 11 with means for flowing coolant therethrough, thereby obviating the need for an aperture and an insert member. These and other variations will be apparent to those skilled in the art and are within the spirit and scope of the invention.

What is claimed is:

1. A method for concentrating a selected element of a sample in a furnace or electrothermal atomizer for atomic spectroscopy, comprising the steps of:
    (a) heating the sample to a temperature above the vaporization temperature of such a selected element;
    (b) maintaining by flow of a coolant a selected location of such a furnace or atomizer at a temperature below the vaporization temperature of the selected element to condense such a selected element at the selected location; and
    (c) heating the selected location in order to vaporize the selected element for measurement by spectroscopy.

2. The method of claim 1 in which the furnace is heated to a sufficient temperature to substantially effect thermal dissociation of undesirable molecular species from the selected element prior to the performance of step (c).

3. The method of claim 1 characterized by removing the volatile portion of the sample from the furnace or atomizer prior to the performance of step (c).

4. An apparatus for concentrating a selected element of a sample for atomic spectroscopy, comprising:
    a heating receptacle comprised of material capable of withstanding the temperatures of atomization of such a sample;
    means for heating the receptacle to the temperatures of atomization for such a sample; and
    means for selectively cooling with a coolant a selected location of the receptacle to a desired temperature.

5. The apparatus of claim 4 wherein the heating receptacle is a graphite furnace tube.

6. The apparatus of claim 4 wherein the heating receptacle is an electrothermal atomizer tube.

7. An apparatus for concentrating a selected element of a sample for atomic spectroscopy, comprising:
    a heating receptacle comprised of material capable of withstanding the temperatures of atomization of such a sample;
    means for heating the receptacle to the temperatures of atomization for such a sample; and
    means for selectively cooling a selected location of the receptacle to a desired temperature, the cooling means including:
        an insert member mounted in a wall of the receptacle to provide a condensation location for such a selected element, the insert member having a coolant chamber disposed therein; and
        flow means for selectively passing a coolant through the coolant chamber in order to selective cool the insert member to such a desired temperature.

8. The apparatus of claim 7 wherein said insert member comprises a cylindrical tube extending through the receptacle, the tube having a bore extending therethrough to act as a chamber for such a coolant.

* * * * *

UNITED STATES PATENT AND TRADEMARK OFFICE
CERTIFICATE OF CORRECTION

PATENT NO. : 4,529,307
DATED : July 16, 1985
INVENTOR(S) : James A. Holcombe and Thomas Rettberg It is certified that error appears in the above-identified patent and that said Letters Patent is hereby corrected as shown below:

In Column 6, lines 49-50, delete "selective" and insert
--selectively--.

Signed and Sealed this

Fifth Day of November 1985

[SEAL]

Attest:

Attesting Officer

DONALD J. QUIGG

Commissioner of Patents and Trademarks